United States Patent [19]

Donaldson et al.

[11] Patent Number: 5,674,196
[45] Date of Patent: Oct. 7, 1997

[54] DEVICE FOR INTRODUCING MEDICAL FLUID INTO THE HUMAN EAR

[76] Inventors: John Donaldson, 3487 Broadway, Fort Myers, Fla. 33901; Krista Donaldson, 117 Centre, Mountain View, Calif. 94041

[21] Appl. No.: 583,342

[22] Filed: Jan. 5, 1996

[51] Int. Cl.[6] ............................................. A61M 11/00
[52] U.S. Cl. ........................... 604/93; 604/28; 604/45; 604/174; 604/256; 607/136
[58] Field of Search ............................ 604/20–21, 27, 604/30, 43, 45, 48, 93, 117, 173–5, 177, 246, 256, 264, 275, 278, 285, 905, 49, 51, 54; 607/115–6, 136–7; 128/864, 866; 4/295; D24/106, 108, 112

[56] References Cited

U.S. PATENT DOCUMENTS

| | | | |
|---|---|---|---|
| 3,783,864 | 1/1974 | Moller | 128/864 |
| 3,991,755 | 11/1976 | Vernon et al. | 607/136 |
| 4,055,233 | 10/1977 | Huntress | 128/864 |
| 4,564,009 | 1/1986 | Brinkhoff | 128/864 |
| 4,706,682 | 11/1987 | Stypulkowski et al. | 607/116 |
| 4,974,606 | 12/1990 | Van Mierlo | 128/864 |
| 5,036,992 | 8/1991 | Mouchawar et al. | 215/307 |
| 5,176,654 | 1/1993 | Schreiber | 604/187 |
| 5,364,343 | 11/1994 | Apolet et al. | 604/43 |
| 5,391,156 | 2/1995 | Hildwein et al. | 604/174 |
| 5,470,320 | 11/1995 | Tiefenbrun et al. | 604/174 |
| 5,476,446 | 12/1995 | Arenburg | 604/54 |

FOREIGN PATENT DOCUMENTS 931191  5/1982  U.S.S.R. ............................ 601/2

*Primary Examiner*—Mark Bockelman
*Assistant Examiner*—Bhisma Mehta
*Attorney, Agent, or Firm*—William E. Noonan

[57] ABSTRACT

A device is provided for administering medical fluid to at least one of the ear canal and the ear drum of a human ear. The device includes an earplug adapted to fit in the ear such that at least a portion of the earplug is snugly received in and substantially seals the ear canal. The earplug has an outer end section proximate the concha of the ear and an inner end section proximate the eardrum. The conduit extends completely through the earplug from the outer end section to the inner end section thereof for introducing medical fluid through the earplug into the ear canal such that the medical fluid is administered to at least one of the ear canal and the eardrum.

17 Claims, 3 Drawing Sheets

DEVICE FOR INTRODUCING MEDICAL FLUID INTO THE HUMAN EAR

SUMMARY OF THE INVENTION

This invention relates to a device for introducing medical fluid into the human ear canal, and, more particularly, to a device for administering topical anesthetic and sterilizing fluids to the eardrum and ear canal.

BACKGROUND OF THE INVENTION

Ear infections are extremely common, particularly among small children. One troubling type of ear infection is inflammation of the middle ear cleft, a condition known as otitis media (OME). Traditionally, ear infections have been treated by antibiotics. Recently, however, new strains of antibiotic resistant bacteria have emerged. As a result, the physician may be required to pierce the eardrum (tympanic membrane) so that the infection can be diagnosed and treated. The procedure known as tympanocentesis involves aspirating middle ear fluid through the eardrum using a needle. A surgical incision or myringotomy may also have to be made into the tympanic membrane to permit insertion of a tympanostomy tube, a device that maintains patency of the eardrum incision. Normally, a tympantocentesis is performed without anesthesia in the doctor's office. However, a myringotomy usually requires some form of anesthesia. When children are involved, a general anesthetic usually must be administered in a hospital operating room.

Employing a general anesthetic for the purpose of diagnosing and treating an ear infection, is relatively expensive and presents additional risks of complications. Local or topical anesthetics have been used in an attempt to reduce this cost and risk. However, problems are experienced when these types of anesthetics are employed, particularly in the case of small children. For one thing, local anesthesia usually requires a painful injection into a very sensitive area of the ear (i.e. the eardrum or ear canal). Topical anesthesia, on the other hand, typically necessitates an undisturbed contact time with the eardrum of 15–60 minutes. This duration is reduced using an iontophoretic process.

In the latter technique, lidocaine and adrenaline are introduced into the ear canal and ionized so that the eardrum is anesthetized. The iontophoretic process requires only about 15 minutes per ear. However, few small children are cooperative enough to remain still in a supine position for a period long enough to accomplish effective anesthesia of the eardrum. Such patients tend to fidget and move. Premature movement can hinder the application of effective (anesthesia) and can cause burns in the ear canal due to movement of the electrodes used in the system. As a result, this usually effective topical anesthetic is generally impractical for use in children, the population at highest risk for middle ear cleft inflammations.

To date, no medical devices have been available to effectively seal the ear canal so that a topical anesthetic or a sterilizing fluid can be administered to the ear canal and eardrum. Likewise, no conventional devices hold the fluid and/or electrodes of an iontophoretic system in place for a prolonged period so that effective anesthesia or sterilization is achieved.

SUMMARY OF THE INVENTION

It is therefore an object of this invention to provide a device for safely and effectively introducing medical fluids, such as anesthetics and sterilization fluids, into the human ear canal so that ear infections can be effectively diagnosed and treated without employing a general anesthetic.

It is a further object of this invention to provide a medical device for holding anesthetic and sterilization fluids in place in the ear canal for extended time periods so that effective anesthesia or sterilization is accomplished, even where the patient prematurely moves or fidgets.

It is a further object of this invention to provide a medical device that permits a patient to move about while a topical sterilization or anesthetic fluid is being administered to the eardrum and ear canal.

It is a further object of this invention to provide a medical device which holds the electrodes of an iontophoretic system safely and securely in place within the human ear canal so that topical anesthesia is attained and which effectively holds the electrodes of the system away from the skin so that burns are avoided.

It is a further object of this invention to provide a medical device which permits the eardrum to be anesthetized topically without requiring an expensive, risky or painful general anesthetic.

It is a further object of this invention to provide a medical device which is an effective adjunct in the diagnosis and treatment of ear infections in small children.

It is a further object of this invention to provide a medical device that permits medical fluids to be safely and effectively administered to both ears simultaneously.

It is a further object of this invention to provide a medical device that may be used effectively with the known methods of topical sterilization and anesthetization.

It is a further object of this invention to provide a medical device that fits comfortably and securely within a patient's ear for an extended time period and which may be manufactured for patients of all ages and ear sizes.

This invention results from a realization that the topical administration of medical fluids to the eardrum and ear canal will be greatly facilitated by using a plug to seal the ear canal so that such fluids are held in place therein for a desired time period. This invention results from the further realization that by providing a suitable channel through such an earplug, the appropriate medical fluid may be effectively introduced into the ear canal through the channel.

This invention features a device for administering medical fluid to at least one of the ear canal and eardrum of a human ear. The device includes an earplug adapted to fit in the ear such that at least a portion of the earplug is snugly received and substantially seals the ear canal. The earplug has an outer end section proximate the concha of the ear and an inner end proximate the eardrum. Conduit means extend completely through the earplug from the outer end section to the inner end section thereof for introducing medical fluid through the earplug into the ear canal such that the medical fluid is administered to at least one of the ear canal and the eardrum. The conduit may be arranged to provide venting as air within the ear canal is displaced by the medical fluid.

In a preferred embodiment, the earplug is composed of a resilient material that permits the earplug to generally conform to the shape of an ear canal that receives the earplug. The conduit means may include an elongate, fluid transmitting tube formed through the earplug. The conduit means may further include receptacle means formed at an outer end of the tube for engaging and holding a syringe in communication with the tube. The syringe is operated to introduce medical fluid from the syringe into the tube. The tube may extend beyond the inner end section of the earplug to a position proximate the eardrum. Vent means typically extend through the earplug from the outer end section to the inner end section adjacent to the conduit means for releasing air from the ear canal when medical fluid is introduced into the ear canal through the conduit means.

At least one flange member may be attached to the earplug and engage a portion of the external ear to assist holding the earplug in place. Each flange member may carry an adhesive that secures the earplug to the engaged portion of the ear. Preferably, an interior flange member is attached to the earplug for engaging the tragus of the ear and a posterior flange member is attached to the earplug for engaging the concha of the ear. A flange collar may unitarily interconnect the flange members. The flange collar surrounds and is attached to the earplug. A peripheral groove is typically formed in the earplug for accommodating the flange collar. Cap means may be provided for covering at least one of the tube and the vent after medical fluid is introduced to the ear canal. The inner end section of the earplug may have a concave surface to ensure complete filling of the canal and displacement of all air.

An obturator apparatus may be engaged with the conduit means after medical fluid is introduced therethrough. The obturator apparatus includes a fitting that is engaged with the receptacle means, and an electrode device carried by the fitting and extending through the conduit means and beyond the inner end section of the earplug and terminating proximate the eardrum. There are means for selectively energizing the electrode device to perform iontophoresis on at least one of the eardrum and ear canal. The electrode device may include a pair of spaced apart wire electrodes and protective insulation formed about the wire electrodes. The fitting and the receptacle means may include corresponding markings that are aligned when the fitting is engaged with the receptacle means to properly orient the obturator apparatus relative to the conduit means.

Figure 1:
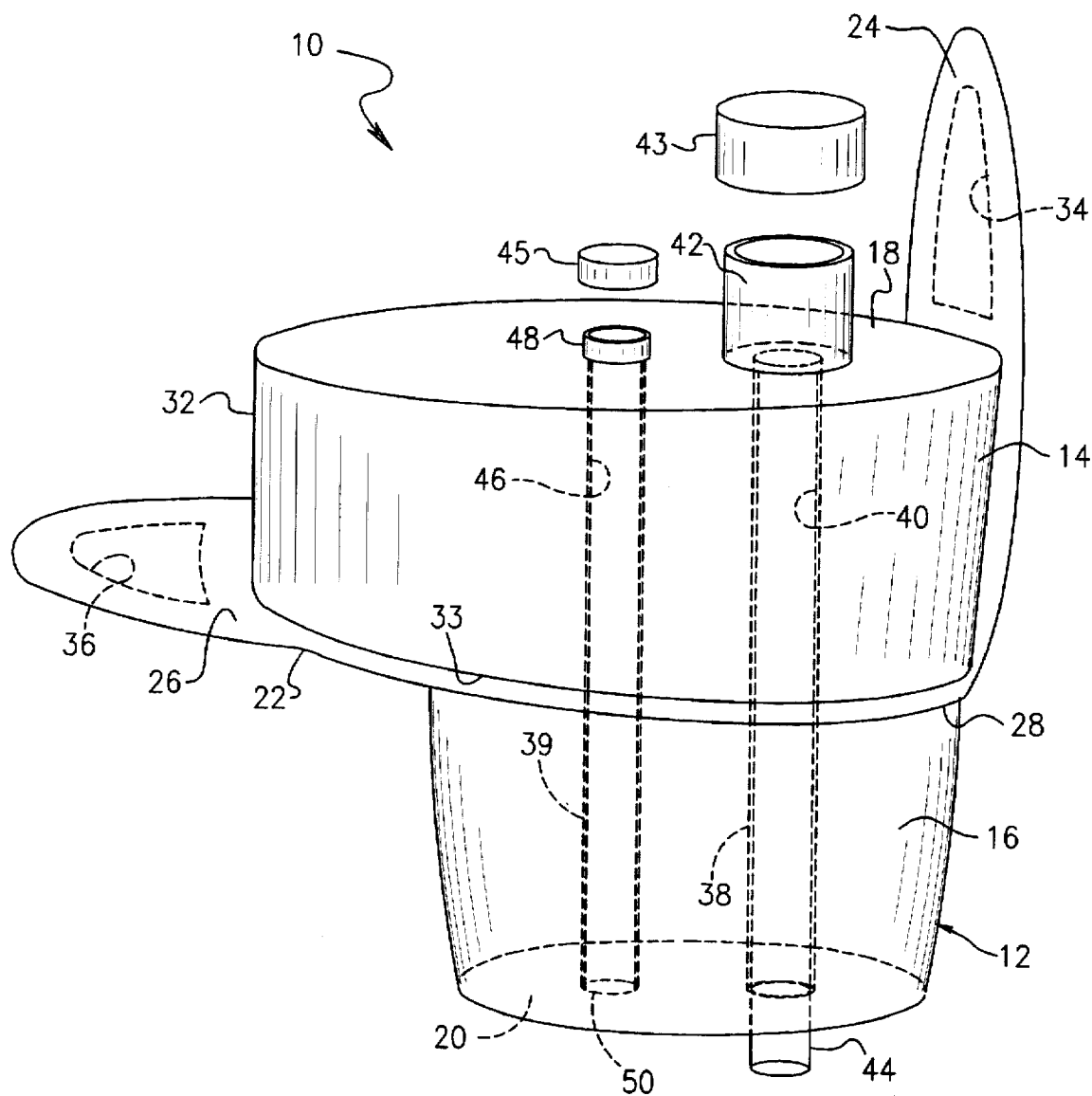
FIG. 1 is a perspective view of a preferred device for introducing medical fluids into the ear canal in accordance with this invention.

There is shown in FIG. 1 a device 10 that is employed according to this invention to introduce medical fluids into a patient's ear canal so that such fluids may be administered to at least one of the ear canal and the eardrum. These medical fluids typically comprise fluids of the types conventionally used to topically sterilize or anesthetize the patient's eardrum and ear canal. Device 10 includes an earplug 12 having a relatively large diameter upper portion 14 and a relatively small diameter lower portion 16. An outer end surface 18 is formed on upper portion 14 and an inner end surface 20 is formed on lower portion 16. The inner end surface is concave. Lower portion 16 of earplug 12 is offset against upper portion 14 such that upper portion 14 includes a posterior section 32 that projects in a left-hand direction. The opposite sides of upper and lower portions 14 and 16 define an anterior section of the earplug. The upper and lower portions 14 and 16 are normally unitarily interconnected and comprise a resilient, form fitting material such as a soft molded foam or Silastic™, that is comfortable when worn in a patient's ear. The earplug material should be waterproof and resistant to organic solvents. Normally, portions 14 and 16 of earplug 12 are formed in one piece by a conventional molding process. Various types of suitable materials may be employed. Alternatively, upper and lower portions 14 and 16 may be formed separately and interconnected by an appropriate adhesive or by heat welding.

Figure 2:
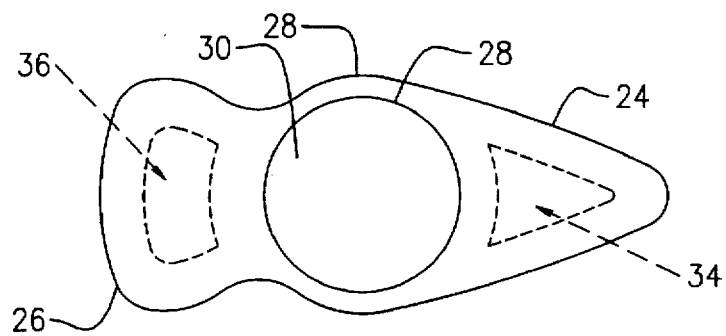
FIG. 2 is a plan view of the flange component in a flattened condition.

A one-piece flange component 22, shown alone in FIG. 2, is attached to and carried by earplug 12. Flange component 22 includes a pair of elongate anterior and posterior flange members 24 and 26, respectively. These flange members are unitarily interconnected by a generally annular flange collar 28, having a central opening 30. Earplug 12, FIG. 1, includes an annular groove 33 that is circumferentially interengaged by collar 28. In other words, opening 30 of flange component 22 receives earplug 12. An appropriate adhesive may be utilized to hold the flange element in place on the earplug. As shown in FIG. 1, anterior flange member 24 extends generally upwardly (outwardly) relative to the earplug and is formed along the anterior side of the ear plug. Posterior flange member 26 extends laterally beneath projecting section 32 of upper plug portion 14 and from the posterior side of earplug 12. Flange component 28 is composed of a moderately stiff, yet flexible plastic material of the type normally employed for medical and surgical applications. As a result, flange elements 24 and 26 can be bent, folded, curved and otherwise configured along the broken line A—A of FIG. 2 engage the patient's ear and assist in attaching earplug 12 to the ear. An optional adhesive 34 is carried by the outer surface of flange member 24. Similarly, an adhesive 36 may be carried by the lower surface of posterior flange member 26.

An elongate channel 38 is formed vertically through earplug element 12. Channel 38 extends completely through upper and lower portions 14 and 16 of the earplug and elongate conduit 40 is disposed through channel 38. The upper or outer end of conduit 40 is communicably connected to a generally cylindrical fitting or receptacle 42 that is constructed so that it is communicably and operably engageable with a standard syringe. A lower end portion 44 of conduit 40 extends slightly beyond inner surface 20 of earplug 12.

An elongate vent tube 46 is similarly formed through a channel 39 in earplug 12 adjacent to conduit 40. Vent tube 46 extends vertically through the earplug from outer surface 18 to inner surface 20. A fitting 48 is formed at the upper end of tube 46 above surface 18. The lower end of tube 46 includes an opening 50 formed in inner surface 20. Both conduit 40 and tube 46 are preferably introduced through performed channels in earplug 12 and have a close tolerance fit within their respective channels. In alternative embodiments, conduit 40 and vent tube 46 may be formed through a single vertical channel in the earplug. Vent tube 46 typically has a smaller diameter than conduit 40. A pair of cylindrical caps 43 and 45 are employed to selectively cover and plug receptacle 42 and fitting 48, respectively. These caps are attached after medical fluid has been injected in accordance with the manner described more fully below.

Figure 3:
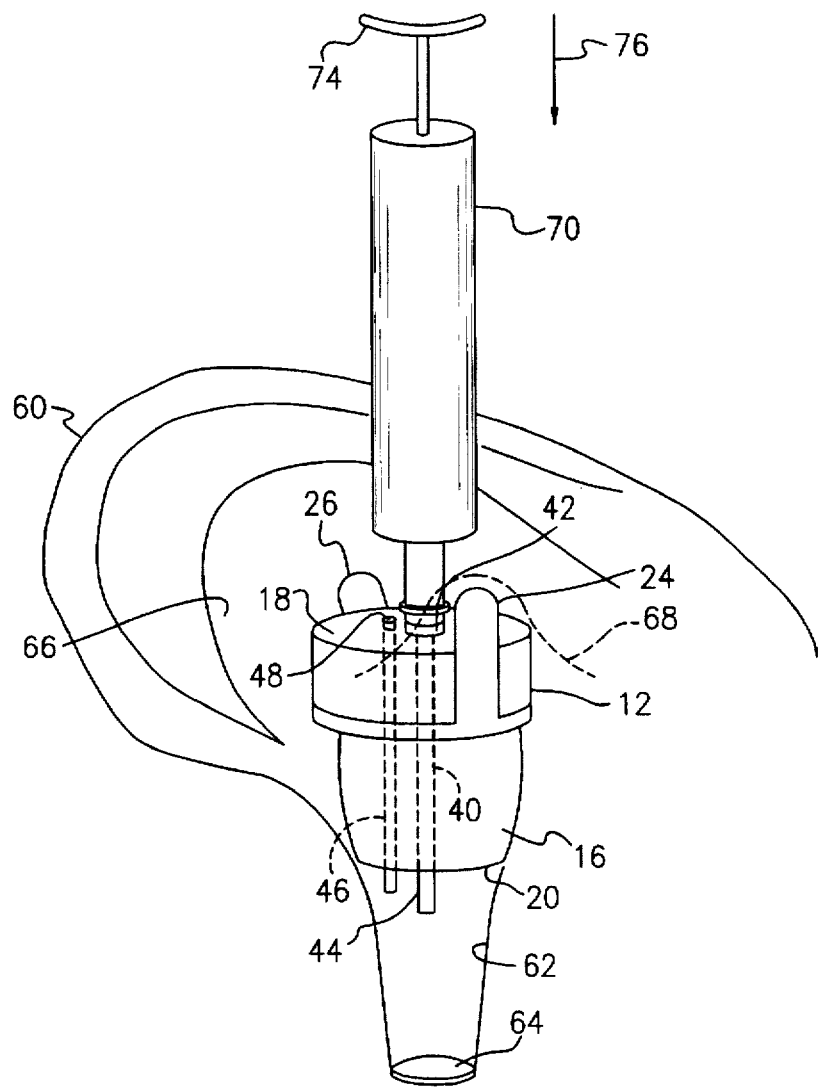
FIG. 3 is a perspective view of the device inserted into the ear canal and engaged by a syringe for injecting medical fluid through the apparatus and into the ear canal.

Earplug 12 is operably interengaged with a patient's ear canal in the manner illustrated in FIG. 3. Before the earplug is placed in the patient's ear, the physician cleans the ear canal of cerumen and debris and examines the tympanic membrane under magnification. Pneumatic otoscopy is employed to confirm that the eardrum is intact. The patient is then placed in a supine position so that his or her ear faces generally upwardly, as illustrated in FIG. 3. The physician then manipulates earplug 12 and inserts it into ear canal 62 of ear 60. Earplug portion 16 has a form fitting shape that generally conforms to the shape of the ear canal so that a relatively snug seal is formed therein. Inner end surface 20 of earplug 12 is oriented relatively proximate eardrum 64. Outer surface 18 is disposed relatively proximate the concha 66 of ear 60. Conduit 40 is located relatively anterior to vent tube 46. This provides additional clearance of conduit 40 from ear drum 64. The earplug is held securely in place by attaching flange members 24 and 26 to associated portions of ear 60. In particular, flexible anterior flange member 24 is manipulated and engaged with tragus 68, shown in phantom. If an adhesive is used, that adhesive helps to hold the anterior flange member against the tragus. By the same token, posterior flange member 26 is curved somewhat upwardly and configured to engage the ear's concha 66. Again, adhesive on the lower surface of flange member 26 helps to hold that flange member against the concha. Earplug 12 is now engaged securely with the ear 60 and ear canal 62 so that administration of medical fluids may be performed.

To introduce an appropriate sterilizing or anesthetic fluid into ear canal 62, a standard medical syringe 70 is interenegaged with earplug 12. Specifically, the hub of the syringe is introduced through receptacle 42 into conduit 40. The receptacle is configured so that it serves as a fitting for securely and communicably receiving syringe 70. As a result, the syringe is held securely in place and extends from earplug 12 and outwardly from ear 60. Topical anesthetic or sterilizing fluid is then injected into the ear canal by depressing syringe plunger 74 in the direction of arrow 76. This introduces the topical fluid into conduit 40. The conduit has a diameter that is sufficiently small so that the fluid slowly passes through the conduit. The medical fluid is eventually discharged from lower end portion 44 into ear canal 62. As a result, the fluid is topically applied to the eardrum 64 and/or ear canal 62, as required. As the fluid is introduced, the air in the ear canal is exhausted through vent tube 46. This procedure continues until medical fluid flows from the upper end of vent tube 46. Normally, the volume of the fluid introduced is sufficient to fill the space between eardrum 64 and inner surface 20 of earplug 12. Because conduit 40 includes a lower portion 44 that extends below the plug, virtually all of the air is exhausted from the ear canal.

After the medical fluid is injected into the ear canal, syringe 70 is disengaged from plug 12. The head of syringe is removed from receptacle 42 and the needle is removed from conduit 40. Caps 43 and 45, FIG. 1 are then engaged with receptacle 42 and fitting 48, respectively. When more viscous fluids such as oils or creams are employed and the diameter of vent tube 26 is sufficiently small, capping that tube is usually unnecessary. The medical fluid is left in the ear canal for the time required to effect either sterilization or anesthetization. During that time, the patient can move about without disrupting the fluid. After the predetermined time period has passed, earplug 12 is simply removed from the ear canal by grasping flange member 24 and 26 and pulling the entire device 10 out of the ear. The medical fluid is also removed from the ear and device 10 is discarded in an appropriate manner.

Figure 4:
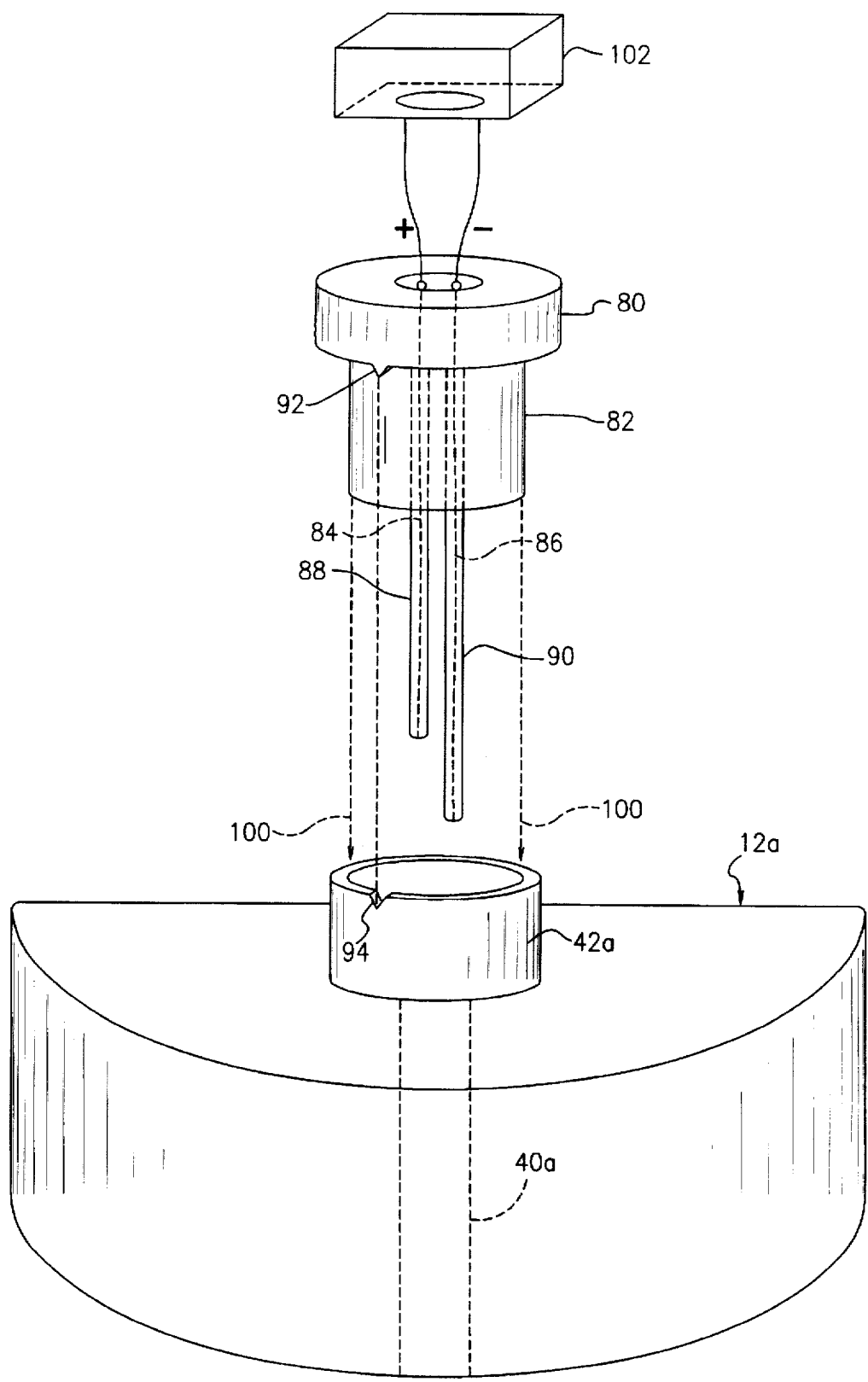
FIG. 4 is an exploded perspective view of an obturator apparatus that is engageable with a receptacle of the conduit means so that iontophoresis may be performed.

In the embodiment of FIG. 4, an obturator apparatus 80 is employed with an earplug 12a so that iontophoretic anesthetization may be performed. Earplug 12a includes only a single vertical channel for accommodating conduit 40a. In this embodiment, no vent tube is used. Otherwise, the earplug is virtually identical to that described in the previous embodiment.

Obturator apparatus 80 includes a fitting 82 that is shaped similarly to a standard syringe head. As a result, fitting 82 may be engaged with and locked into complementary receptacle 42a disposed at the top of conduit 40a. Fitting 82 carries a pair of positive and negative electrodes 84 and 86, respectively. These electrodes are longitudinally covered by respective insulating sheaths 88 and 90. The sheaths keep the electrodes separated and prevent them from engaging the ear canal skin. Additionally, electrodes 84 and 86 are vertically separated, with negative electrode 86 being somewhat longer than positive electrode 84. The electrodes are connected by an adapter 102 to the appropriate poles of conventional iontophoretic equipment. Such equipment will be understood by those skilled in the art.

The embodiment of FIG. 4 is employed in the following manner. The patient is first prepared as previously described. The physician then inserts earplug 12a into the patient's ear canal, again in accordance with the previously described embodiment. A thin catheter, not shown, is introduced into receptacle 42a and conduit 40a and predetermined dosage of iontophoretic fluid, for example, a mixture of lidocaine and adrenaline, is introduced through the catheter into conduit 40a and from there into the ear canal. As this anesthetic fluid is introduced, air in the ear canal is vented through conduit 40a and, in particular, through the space between the conduit and the catheter. When the fluid overflows conduit 40a and receptacle 42a, the physician is signaled that all of the air has been exhausted from the ear canal. The catheter is then removed from conduit 40a and replaced by obturator apparatus 80.

In particular, the obturator apparatus is lowered in the direction of arrows 100 such that fitting 82 is operably engaged with receptacle 42a. The fitting and receptacle carry corresponding markings including a detente 92 carried by fitting 82 and a notch 94 formed in receptacle 42a. These markings are aligned so that the electrodes 84 and 86 of obturator 80 are properly aligned in the ear canal. Specifically, the electrodes pass through earplug 12a and into the iontophoretic fluid previously introduced into the ear canal. The electrodes are then activated so that iontophorosis is performed in a known manner. Lidocaine hydrochloride and adrenaline HCl are ionized and the eardrum is effectively anesthetized. The process takes about 15 minutes. During that time, earplug 12a holds the electrodes of the obturator apparatus securely in place. The patient can move around without disrupting the electrodes or spilling the medical fluid from their ear.

Both ears may undergo iontophoresis simultaneously. This can be achieved by mounting a pair of obturators at opposite ends of a headset. The headset retains and organizes the wires that interconnect the iontophoresis generator with the electrodes of each obturator. The headset is placed on the patient's head and each obturator is engaged with a respective ear canal in the manner previously described.

After anesthesia is achieved, the obturator apparatus 80 is disengaged from earplug 12a by lifting it upwardly from the earplug. The earplug itself is then removed from the ear and the anesthetic fluid is likewise removed as previously described.

The present invention therefore permits medical fluids to be safely and effectively introduced into the ear canal and held securely therein for a predetermined period of time so that topical anesthetization or sterilization is accomplished. The device seals these fluids securely in place in the ear canal, even if the patient moves or fidgets. As a result, the invention is particularly effective for use with small children. Additionally, the device permits the widespread and increased use of topical anesthetics within the ear. This avoids the discomfort of hypodermic injections into the eardrum and significantly reduces the need to use general anesthetic techniques for treatment of the eardrum and middle ear. As a result, the cost and risks associated with general anesthesia are eliminated. The device can be manufactured in various standard sizes and can be used by patients of all ages. The device may be marketed separately or in kits containing sterilization and/or anesthetic fluids. It may also be available as part of an iontophoretic system.

What is claimed is:

1. A device for administering medical fluid to at least one of the ear canal and eardrum of a human ear, said device comprising:

an earplug adapted to fit in the ear such that at least a portion of said earplug is snugly received in and substantially seals the ear canal, said earplug having an outer end section proximate the concha of the ear and an inner end section proximate the eardrum;

anterior and posterior flange members attached to said earplug and engaging the tragus and concha, respectively, of the ear to assist holding said earplug in place;

a flange collar that unitarily interconnects said flange members, said flange collar surrounding and being attached to said earplug, said earplug including a peripheral groove for accommodating said flange collar; and conduit means extending completely through said earplug from said outer end section to said inner end section thereof for introducing medical fluid through said earplug into the ear canal such that the medical fluid is administered to at least one of the ear canal and the eardrum.

2. The device of claim 1 in which said conduit means include an elongate, fluid transmitting tube formed through said earplug.

3. The device of claim 2 in which said conduit means further include receptacle means formed at an outer end of said tube for engaging and holding a syringe in communication with said tube such that the syringe may be operated to introduce medical fluid from the syringe into said tube.

4. The device of claim 3 in which said tube extends beyond the inner end section of said earplug to a position proximate the eardrum.

5. The device of claim 3 further including an obturator apparatus that is engaged with said conduit means after medical fluid is introduced therethrough, said obturator apparatus including a fitting that is engaged with said receptacle means, an electrode device carried by said fitting, said electrode device extending through said conduit means and beyond the inner end section of said earplug and terminating proximate the eardrum; and means for selectively energizing said electrode device to perform iontophoresis on at least one of the eardrum and ear canal.

6. The device of claim 1 further including vent means which extends through said earplug from said outer end section to said inner end section adjacent to said conduit means for releasing air from the ear canal when medical fluid is introduced into the ear canal through said conduit means.

7. The device of claim 6 further including means for capping at least one of said conduit means and said vent means after medical fluid is introduced to the ear canal.

8. The device of claim 1 in which said earplug is composed of a resilient material such that said earplug generally conforms to the shape of an ear canal which receives said earplug.

9. The device of claim 1 in which at least one said flange member carries an adhesive that secures said earplug to said engaged portion of the ear.

10. A device for administering medical fluid to at least one of the ear canal and ear drum of a human ear, said device comprising:

an earplug adapted to fit in the ear such that at least a portion of said earplug is snugly received in and substantially seals the ear canal, said earplug having an outer end section proximate the concha of the ear and an inner end section proximate the ear drum;

conduit means extending completely through said earplug from said outer end section to said inner end section thereof for introducing medical fluid through said earplug into the ear canal such that the medical fluid is administered to at least one of the ear canal and the ear drum, conduit means including an elongate, fluid transmitting tube formed through said earplug, said conduit means further including receptacle means formed at an outer end of said tube for engaging and holding a syringe in communication with said tube such that the syringe may be operated to introduce medical fluid from the syringe into said tube;

an obturator apparatus that is engaged with said conduit means after medical fluid is introduced therethrough, said obturator apparatus including a fitting that is engaged with said receptacle means and an electrode device carried by said fitting, said electrode device extending through said conduit means and beyond the inner end of said earplug and terminating proximate the eardrum; and means for selectively energizing said electrode device to perform iontophoresis on at least one of the ear drum and the ear canal.

11. The deice of claim 10 in which said electrode deice includes a pair of space apart wire electrodes and protective insulation formed about said wire electrodes.

12. The device of claim 10 in which said fitting carries a first marking and said receptacle means carries a corresponding second marking, said first and second markings being alignable when the fitting is engaged with said receptacle means to properly orient said obturator apparatus relative to said conduit means and align said electrode device within the ear canal.

13. The device of claim 12 in which one of said first and second markings includes a detent and the other of said first and second markings includes a complementary notch.

14. A method for administering medical fluid to at least one of the ear canal and ear drum of a human ear, said method comprising the steps of:

providing an earplug adapted to fit in a human ear and having a relatively wide outer end section, a relatively narrow inner end section and a conduit extending completely through the earplug from said outer end section to said inner end section;

forming a vent through the earplug from said outer end section to said inner end section adjacent to said conduit;

inserting said earplug into a human ear such that at least a portion of the earplug is snugly received in and substantially seals the ear canal, said outer end section is disposed proximate the concha of the ear and said inner end section is disposed proximate the ear drum;

introducing medical fluid through said conduit into the ear canal such that the medical fluid is administered to at least one of the ear canal and the ear drum and until said fluid flows from said vent at said outer end section of said earplug; and capping at least one of the conduit and the vent after medical fluid is introduced into the ear canal.

15. The method of claim 14 further including the steps forming an elongate fluid transmitting tube through said earplug to define said conduit, forming a receptacle at an outer end of said tube, interengaging a syringe with said receptacle such that the syringe is in communication with said tube, and operating the syringe to introduce medical fluid from the syringe through the tube and into the ear canal.

16. The method of claim 15 further including the steps of interengaging an obturator apparatus with the conduit after medical fluid is introduced through the conduit, which obturator apparatus includes a fitting that is engaged with the receptacle, and an electrode device carried by the fitting, extending the electrode device through the conduit and beyond the inner end of the earplug such that said electrode device terminates proximate the ear drum and selectively energizing the electrode device to perform iontophoresis on at least one of the ear drum and the ear canal.

17. The method of claim 14 further including the step of allowing the medical fluid to remain in the ear canal with the earplug inserted in the ear for a predetermined time.

* * * * *